US012611193B2

(12) United States Patent
Peng et al.

(10) Patent No.: US 12,611,193 B2
(45) Date of Patent: Apr. 28, 2026

(54) IMAGING TISSUES AND ORGANS BEHIND OBSTACLES USING AN ULTRASOUND ARRAY TRANSDUCER

(71) Applicant: CLOUDSTREAM MEDICAL IMAGING, INC., Houston, TX (US)

(72) Inventors: Chengbin Peng, Houston, TX (US); Jun Tang, Houston, TX (US)

(73) Assignee: CLOUDSTREAM MEDICAL IMAGING, INC., Houston, TX (US)

( * ) Notice: Subject to any disclaimer, the term of this patent is extended or adjusted under 35 U.S.C. 154(b) by 153 days.

(21) Appl. No.: 18/288,376

(22) PCT Filed: Jun. 3, 2022

(86) PCT No.: PCT/US2022/032059

§ 371 (c)(1),
(2) Date: Oct. 25, 2023

(87) PCT Pub. No.: WO2022/260935

PCT Pub. Date: Dec. 15, 2022

(65) Prior Publication Data

US 2024/0206854 A1      Jun. 27, 2024

Related U.S. Application Data

(60) Provisional application No. 63/197,932, filed on Jun. 7, 2021.

(51) Int. Cl.
*A61B 8/00*            (2006.01)

(52) U.S. Cl.
CPC .......... *A61B 8/5269* (2013.01); *A61B 8/4488* (2013.01); *A61B 8/5207* (2013.01)

(58) Field of Classification Search
CPC ..... A61B 8/4488; A61B 8/5269; A61B 8/085; A61B 8/54; G01S 7/52026; G01S 7/52046
See application file for complete search history.

(56) References Cited

U.S. PATENT DOCUMENTS

| | | | |
|---|---|---|---|
| 5,278,757 A * | 1/1994 | Hoctor | G01S 15/8918 |
| | | | 600/463 |
| 5,640,959 A | 6/1997 | Hara et al. | |
| 2009/0152471 A1 | 6/2009 | Rousso et al. | |
| 2010/0056928 A1 | 3/2010 | Zuzak et al. | |
| 2012/0157842 A1 | 6/2012 | Davis et al. | |

(Continued)

*Primary Examiner* — Nyrobi Celestine

(74) *Attorney, Agent, or Firm* — SZDC Law PC

(57) ABSTRACT

A method for imaging tissues behind obstacles includes following steps: (1) providing an ultrasound array transducer that includes at least four active elements; (2) spraying a data sample of an ultrasound beam along an impulse response curve into an output image domain; (3) binning each point on the impulse response curve by a value of an unique attribute; (4) summing an image value at the each point on the impulse response curve into a corresponding partial image volume associated with the unique attribute; (5) repeating steps (2)-(4) for all data samples of all ultrasound beams to obtain a plurality of partial image volumes; (6) sorting the partial image volumes by the unique attribute to generate common image point gathers; and (7) obtaining an image of the tissues by stacking common image point gathers at all output locations.

10 Claims, 9 Drawing Sheets

(56) References Cited

U.S. PATENT DOCUMENTS

| | | | |
|---|---|---|---|
| 2016/0089116 A1* | 3/2016 | Duncan | G01S 15/8977 |
| | | | 600/440 |
| 2017/0039738 A1 | 2/2017 | Ziv et al. | |
| 2018/0088220 A1* | 3/2018 | Flynn | G01S 15/8997 |
| 2018/0300876 A1* | 10/2018 | Mauldin, Jr. | A61B 8/0875 |
| 2019/0104982 A1 | 4/2019 | Dunn et al. | |
| 2019/0192114 A1* | 6/2019 | Mauldin, Jr. | A61B 8/085 |
| 2019/0317054 A1* | 10/2019 | Lopez Villaverde | |
| | | | A61B 8/5269 |
| 2020/0158844 A1* | 5/2020 | Li | A61B 8/54 |
| 2021/0113182 A1* | 4/2021 | Robert | A61B 8/4494 |

* cited by examiner

Scan a common image point gather

Remove dim zones on
the common image point gather

Stack into a single
output trace

IMAGING TISSUES AND ORGANS BEHIND OBSTACLES USING AN ULTRASOUND ARRAY TRANSDUCER

This application is the national stage application of PCT/US2022/032059, filed on Jun. 3, 2022, which claims priority to U.S. Provisional Patent Application No. 63/197,932, filed on Jun. 7, 2021, which is incorporated by reference for all purposes as if fully set forth herein.

FIELD OF THE INVENTION

The present invention relates to a method for imaging tissues and organs behind obstacles using an ultrasound array transducer.

BACKGROUND OF THE INVENTION

Ultrasound imaging is a safe and noninvasive medical test that helps physicians diagnose and treat medical conditions. Ultrasound has difficulty penetrating bones and other hard objects, therefore, can only see the outer surface of bony structures and not what lies within and behind (except in infants who have more cartilage in their skeletons than older children or adults) [3]. A special ultrasound array was reported for bone sonography where a low frequency annular array device was used for image guidance during spinal fusion surgery and the process of pedicle screw insertion [4].

Ultrasound also has difficulty to image a region of interest containing mineralized tissues such as a kidney stone. For example, in publication [5], a border and a shadow based on image segmentation were defined and the size of the kidney stone was calculated. An interactive visual guidance tool (in a "V" shape) was used to detect and spatially define the blockage of ribs in a field of view of an ultrasound imaging acquisition and display system [6, 8]. Other shadow suppression technique was also used to reduce fork-like image artifacts, for example, by weighting down some steering directions of ultrasound beams [7]. All these methods are for identification of shadows or blockages caused by shallow high impedance obstacles, without offering a solution to image behind rib cage and other hard objects.

A commercial linear phased array transducer (or simply phased array) can be used to image tissues and organs behind a rib cage [1, 3]. This transducer is short in length so that it can be placed in between rib bones along certain directions. All elements are used to obtain images at each scan line. Because the sound beams are steered at varying angles from one side of the transducer to the other, a sector image output is produced. The scan lines are fan-like, causing the line density to decrease with depth, resulting in loss of both resolution and signal to noise ratio. The focusing capabilities of phased array transducers in the periphery of the image are also very limited.

The present invention relates to ultrasound imaging in the presence of shallow rib bones or other high impedance obstacles (e.g., metal implants). In particular, the invention addresses two urgent needs in medical diagnostic imaging of tissues and organs behind these obstacles: (1) much better resolution and signal to noise ratio, and (2) ability to place an ultrasound scanner in any position and direction without fear of creating shadow zones in output images.

Longer ultrasound sound arrays are needed in order to further improve image resolution for cardiovascular applications because the heart organ is deep behind the rib cage and conventional phased arrays are short in length compared to the depth of examination. In some other scenarios a physician sometime wants to look at a particular feature from certain locations and in certain directions but presence of rib bones causes difficulties because the current ultrasound scanners are not able to produce acceptable images at these locations and directions. The ability to use a longer ultrasound array and the ability to place the array at any location over the rib cage and in any direction make our invention useful and desirable for cardiovascular applications.

SUMMARY OF THE INVENTION

In one embodiment, the present application discloses a method for imaging tissues behind obstacles that includes following steps: (1) providing an ultrasound array transducer that includes at least four active elements; (2) spraying a data sample of an ultrasound beam along an impulse response curve into an output image domain; (3) binning each point on the impulse response curve by a value of an unique attribute; (4) summing an image value at the each point on the impulse response curve into a corresponding partial image volume associated with the unique attribute; (5) repeating steps (2)-(4) for all data samples of all ultrasound beams to obtain a plurality of partial image volumes; (6) sorting the partial image volumes by the unique attribute to generate common image point gathers; and (7) obtaining an image of the tissues by stacking common image point gathers at all output locations.

In another embodiment, the ultrasound array transducer is a linear array transducer, a curved array transducer, or a phased array transducer.

In another embodiment, the ultrasound array transducer includes more than one row of active elements.

In another embodiment, the unique attribute is a transmitter-receiver distance on the ultrasound array transducer or a reflection angle at an image point.

In another embodiment, the unique attribute is a function of element positions on the ultrasound array transducer and/or scattering directions at an image point.

In another embodiment, the method further includes after generating the common image point gathers, performing a scan of amplitude variations on each common image point gather and determining dim zones on the each common image point gather; and excluding or weighting down the dim zones in stacking the common image point gathers.

In another embodiment, the dim zones on the each common image point gather are caused by loss of transmitted energies when the ultrasound beam is blocked by the obstacles.

In another embodiment, the dim zones on the each common image point gather are determined by measuring an envelope amplitude, an acoustic energy level, or a signal coherency.

In another embodiment, the method further includes after generating the partial image volumes, performing a scan of amplitude variations on each partial image volume and determining dim zones on the partial image volumes; and excluding or weighting down the dim zones in subsequent coherent compounding of the partial image volumes.

In another embodiment, the dim zones on the each partial image volume are caused by loss of transmitted energies when the ultrasound beam is blocked by the obstacles.

In another embodiment, the dim zones on a partial image volume are determined by measuring in envelope amplitude.

In another embodiment, the dim zones on the each partial image volume are determined by measuring an acoustic energy level or a signal coherency.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Reference will now be made in detail to embodiments of the present invention, example of which is illustrated in the accompanying drawings.

Part I: Impulse Responses of Ultrasound Beam Data

Figure 1:
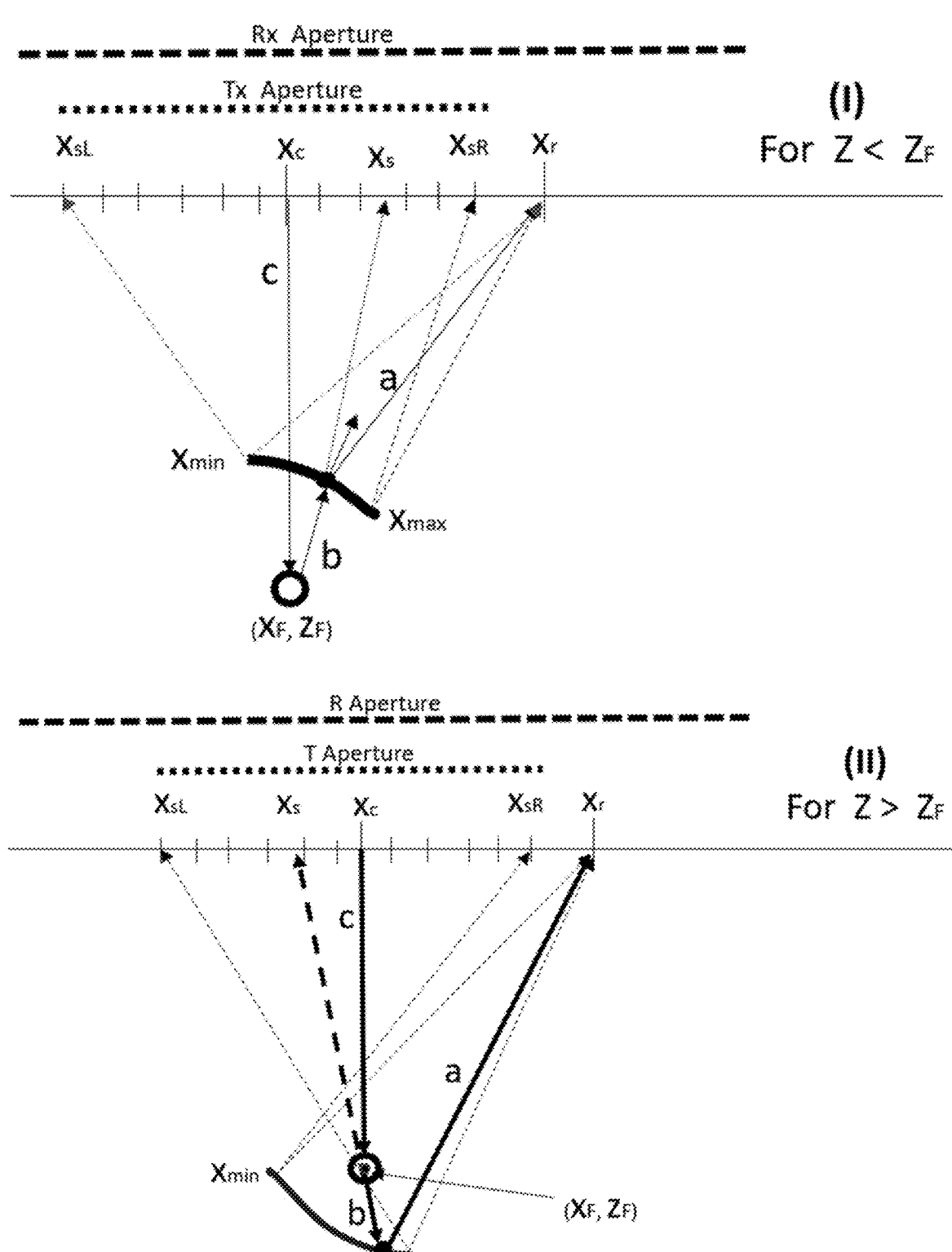
FIG. 1 depicts one impulse response for a focused beam with a Tx aperture of active transmitters and a Rx aperture of active receivers. An impulse response of a beamforming operator is a curve (thick line) that contains all possible image points that one sample in a beam record contributes to. The curve has a finite support from $[X_{min}, X_{max}]$. The open circle is the focal point for this beam. The solid black dot on the thick line is an output image point (x, z). Here $X_c$ is the beam center coordinate. $X_r$ is the receiver coordinate for this data sample. $X_s$ is the stationary phase solution of the effective transmitter coordinate. Offset H is the distance between $X_r$ and $X_s$. Reflection angle is half of the intersection angle between a line from $X_s$ to (x, z) and another line from $X_r$ to (x, z). Top (I) is for the case $Z<Z_F$. Bottom (II) is for the case $Z>Z_F$.

Traditional beamforming of ultrasound data utilizes dynamic focusing method implemented on FPGA hardware [1-2]. Modern ultrasound imaging applications use pixel-based beamforming methods [9-14], mostly implemented on GPU hardware. All these methods can be easily understood by examining spatial impulse responses of the beamforming operators applied on individual data sample. An impulse response of a beamforming operator, by our definition, is a curve in image domain with a finite support. It contains all possible image points that one sample in one input ultrasound beam data contributes to. The final image is formed by summing all impulse responses for all input data samples and for all beams. FIG. 1 depicts one impulse response for a focused beam (thick curve from $X_{min}$ to $X_{max}$). Similar impulse responses can be produced for divergent beam data and planewave beam data. In FIG. 1, an acquisition layout for one input beam data is shown. Active transmitters are covered by the dot line labeled Tx aperture. Active receivers are covered by the dot line labeled Rx aperture. These two apertures can be the same or different without any impact on our analysis herein. The leftmost transmitter is at $X_{sL}$ and the rightmost transmitter is at $X_sR$. The beam center is at $X_c$. The focal point is at $(X_F, Z_F)$. One data sample recorded by a receiver at $X_r$ is used to generate the impulse response curve. The impulse response curve has a finite support between $[X_{min}, X_{max}]$, indicated by the thick line, beyond which there are no stationary reflections for this data sample. This physical restriction is ignored by all published pixel-based beamforming methods. It is also worthwhile to note that the traditional dynamic focusing method corresponds to a single point on the impulse response curve at the location where it intersects with the scanline of this beam. In this regard, the traditional dynamic focusing method is wasteful in utilizing the ultrasound beam data for imaging because only one point is imaged by a whole beam.

Formulas are given in the shaded box in FIG. 1 for the calculation of the impulse response curve and its spatial support. $X_s$ is the stationary location of a transmitter that makes a significant contribution to the image at the output point (x, z). The distance between $X_s$ and $X_r$ is called the stationary offset, or simply offset. The reflection angle at (x, z) is called the stationary specular reflection angle, or simply reflection angle. Each point on the impulse response curve has distinct values of offset, reflection angle, and dip angle, to name a few (collectively called unique attributes). Partial image volumes can be generated by binning and sorting each point on the impulse response curve according to the value of a unique attribute. In the box, $t_a$ is the travel time from the receiver to the image point, $t_b$ is the travel time from the focal point to the image point, and $t_c$ is the travel time from the focal point to the beam center. The arrival time of the input data sample is t.

A general formulation of impulse response calculation for ultrasound beam data of arbitrary types can be found in our U.S. patent application No. 63/184,174 [15], and its publication is incorporated by references in its entirety.

Part II: Ultrasound Imaging Behind Obstacles

2.1 Common Image Point Gather

Figure 2:
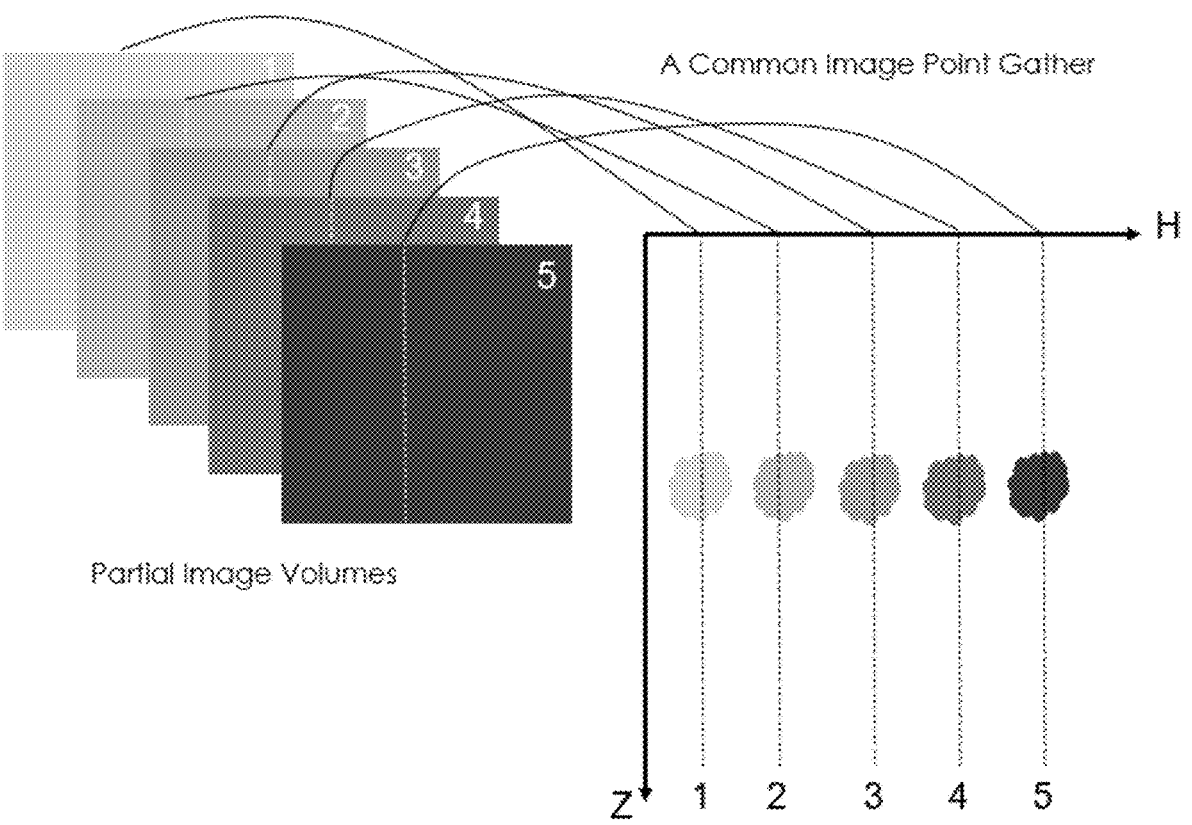
FIG. 2 depicts the formation of a common image point gather: for each fixed lateral position we extract one vertical trace from each partial image volume and put them side by side. This organization of beamformed partial images is called a common image point gather. The vertical axis is image depth (Z) or vertical time. The horizontal axis is the attribute (H) used in the binning of the partial images. The attribute can be either offset or reflection angle, or any other valid parameter. We use the index number of each partial image volume in this illustration. In practice we use the physical value of the binning attribute to label the horizontal axis (e.g., offset H in this cartoon).

A common image point gather is formed by sorting all partial image volumes for a fixed output location into a gather as shown in FIG. 2. A partial image volume is generated during beamforming by binning and sorting each point on an impulse response curve (FIG. 1) according to the value of a unique attribute. The attribute can be offset, reflection angle, scattering angle, or some other quantities (for example, data acquisition settings such as sequence (beam) number, planewave angle, receiver location etc.). The final image is formed by stacking all common image point gathers.

This is a novel method of generating, in ultrasound beamforming, partial image volumes and common image point gathers binned and sorted by transmitter to receiver offsets (at the transducer level) or reflection angles (at an image point). Other imaging methods can be modified, with efforts, to produce similar partial image volumes and common image point gathers. For example, one can modify the Kirchhoff integral method commonly used in geophysics to produce partial image volumes and common image point gathers for ultrasound beam data. The required modification is to spray each data sample onto a family of physically possible Kirchhoff impulse response curves, not onto a single impulse response curve defined by a fixed source location and a fixed receiver location as described in literature [19]. It is worthwhile to note that, if the correct sound speed is used in beamforming, the common image point gather in FIG. 2 shall be flat. In this case the partial images will coherently compound together to produce the final image with enhanced resolution and signal to noise ratio.

2.2 Dim Zones on Common Imaging Point Gathers

Figure 3:
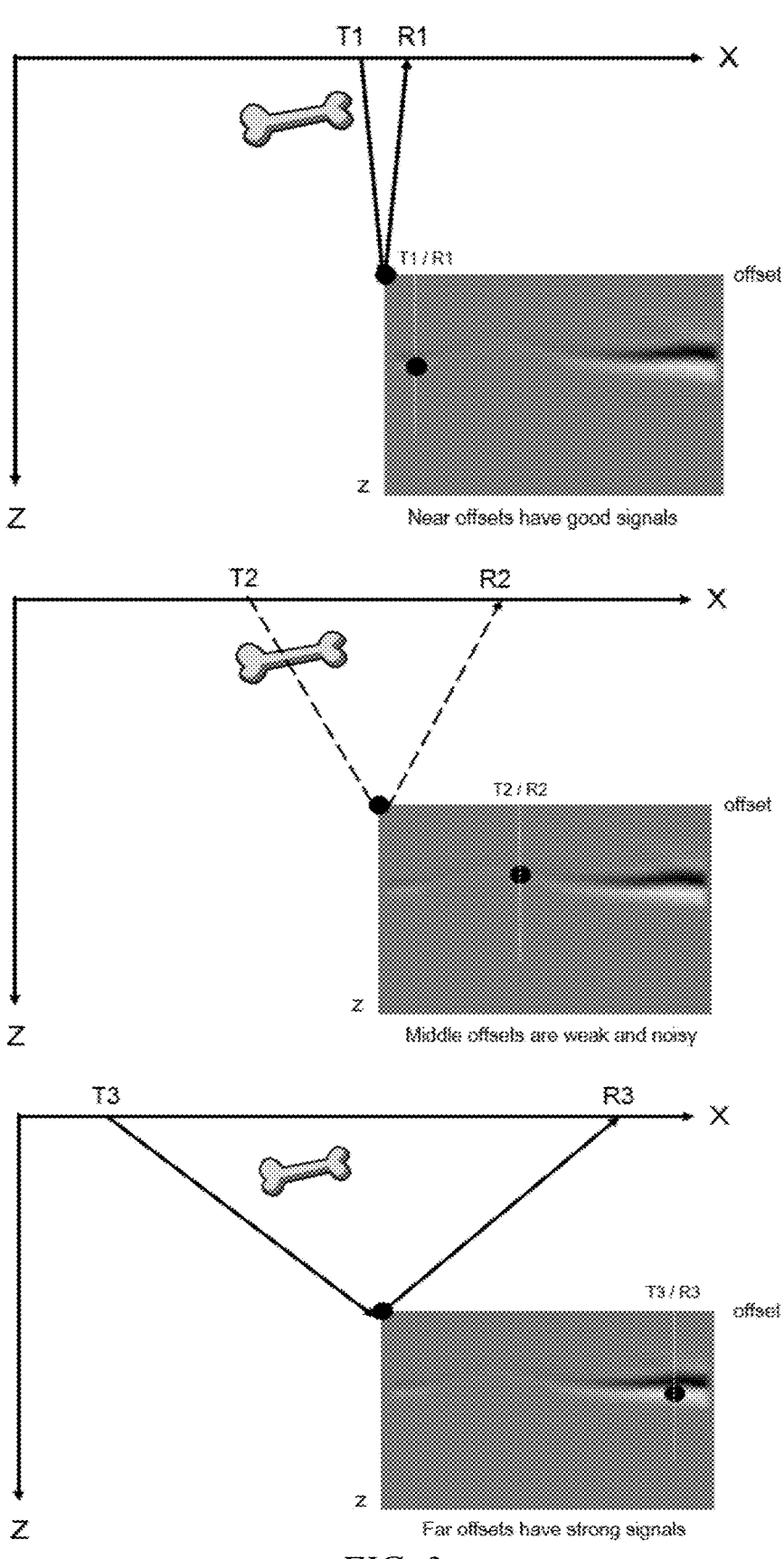
FIG. 3 depicts the causes of dim zones on a common image point gather. A bone is located at shallow depth in the image domain. Top (near offset): inside the common image point gather the solid circle is an image contributed by the ray path pair from transmitter T1 to the scatter and back to the receiver R1. Middle (middle offset): the solid circle is the same image contributed by the ray path pair from transmitter T2 to the scatter and back to the receiver R2. Bottom (far offset): the solid circle is the same image contributed by the ray path pair from transmitter T3 to the scatter and back to the receiver R3. The ray path pair T2/R2 of the middle offset is blocked by the bone at shallow depth, causing deterioration of image quality.

Dim zones seen on a common image point gather are caused by shallow bones or other high impedance objects blocking sound wave propagation either from transmitter to a scatter point or from the scatter point back to a receiver or both, as illustrated in FIG. 3. In this figure, the image domain is the (X, Z) plane. We are looking at one image point (black circle). A bone is located at a shallow depth in the image domain, above the image point. A common image point gather (in offset) is shown at the image point (see the insert). The common image point gather shows a plurality of partial images at the same location, generated by different source and receiver offsets. First let's look at a near-offset image (top, the black circle inside the first insert). It is at an offset that corresponds to the ray path pair from transmitter T1 to the scatter and back to the receiver R1. This pair of ray paths is not blocked by the bone, and as a result, the image signal is well behaved. Second let's look at a middle-offset image (middle, the black circle inside the second insert). The circle is at an offset that corresponds to the ray path pair from transmitter T2 to the scatter and back to the receiver R2. This pair of ray paths is blocked by the bone, causing an image that is weak and mis-positioned. Lastly let's look at a far-offset image (bottom, the black circle inside the third insert). It is at another offset that corresponds to the ray path pair from transmitter T3 to the scatter and back to the receiver R3. This pair of ray paths is not blocked by the bone. As one can see, the image signal is strong and well behaved. Therefore useful contributions to the final image at this location are from both the near-offset partial images and the far-offset partial images. Inclusion of the middle-offset partial images in the formation of the final image (via stacking or coherent compounding) will deteriorate image quality and generate artifacts.

The challenge is, as one moves from location to location, the contributing offsets change. For example, at a location directly beneath a bone near-offset images are poor and error prone. At another location away from the bone far-offset images are poor and error prone. This makes it hard for a beamformer to automatically avoid problematic offsets. The deterioration and artifacts are often seen on images produced by commercial ultrasound scanners when they are placed on top of human rib cages [3].

2.3 Optimal Stacking

Figure 4:
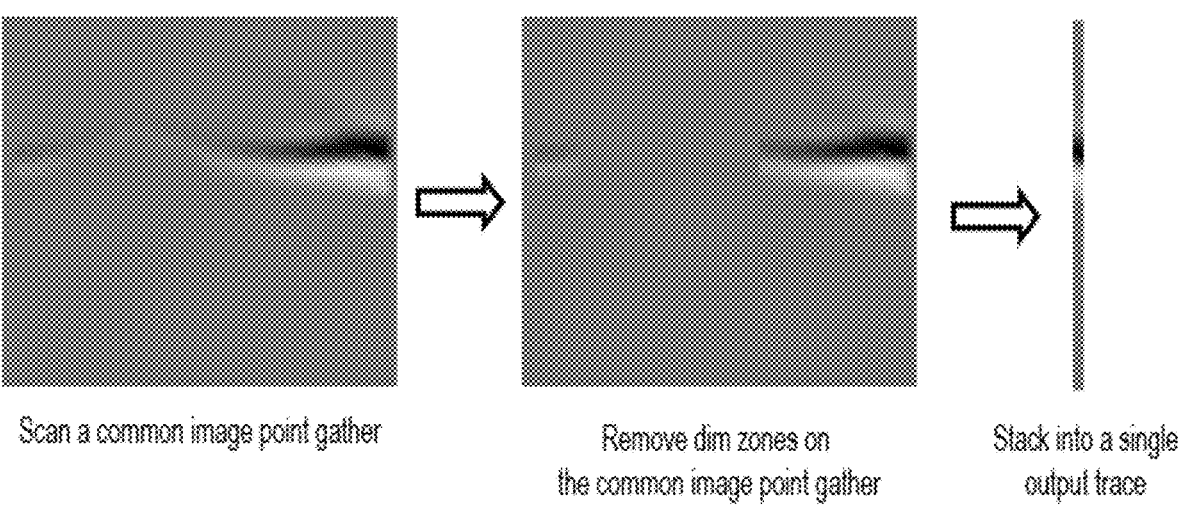
FIG. 4 depicts the optimal stacking of a common image point gather. We first scan the common image gather for dim zones (left). We then set weights inside the dim zones to 0 and outside to 1 (middle). Finally, we perform a weighted stacking of the common image point gather to produce a single trace at this location (right).

The final image is produced by stacking common image point gathers, with optimal weights on contributing offsets. We use envelope amplitudes as a measure of energy level for every trace on a common image point gather. We compare the amplitude of a given trace to the average amplitude of all traces in the data volume. If the envelope amplitude of the trace falls below a certain percentage of the averaged envelope amplitude at a given depth level, we exclude or weight down the image sample in the final stacking or coherent compounding. In so doing we exclude dim zones on a common image point gather as shown in FIG. 4. In this figure a common image point gather at a location near a shallow bone is shown on the left. We set the weights in the dim zone to 0 and outside the dim zones to 1 (middle). The final image value at this location is the weighted sum of the common image point gather normalized by the sum of the weights (right, now a single output trace). In this way all ray paths that are impacted by the shallow rib bone are either excluded or weighted down, as if the bone does not exist in the first place. We then repeat this process for all common image point gathers in order to obtain the final image volume.

Other measures of quantifying dim zones can also be used, such as absolute amplitude, energy, coherency, and any combination of them. Other weighting schemes can also be used such as smaller weights inside the dim zones and larger weights outside the dim zones.

Figure 5:
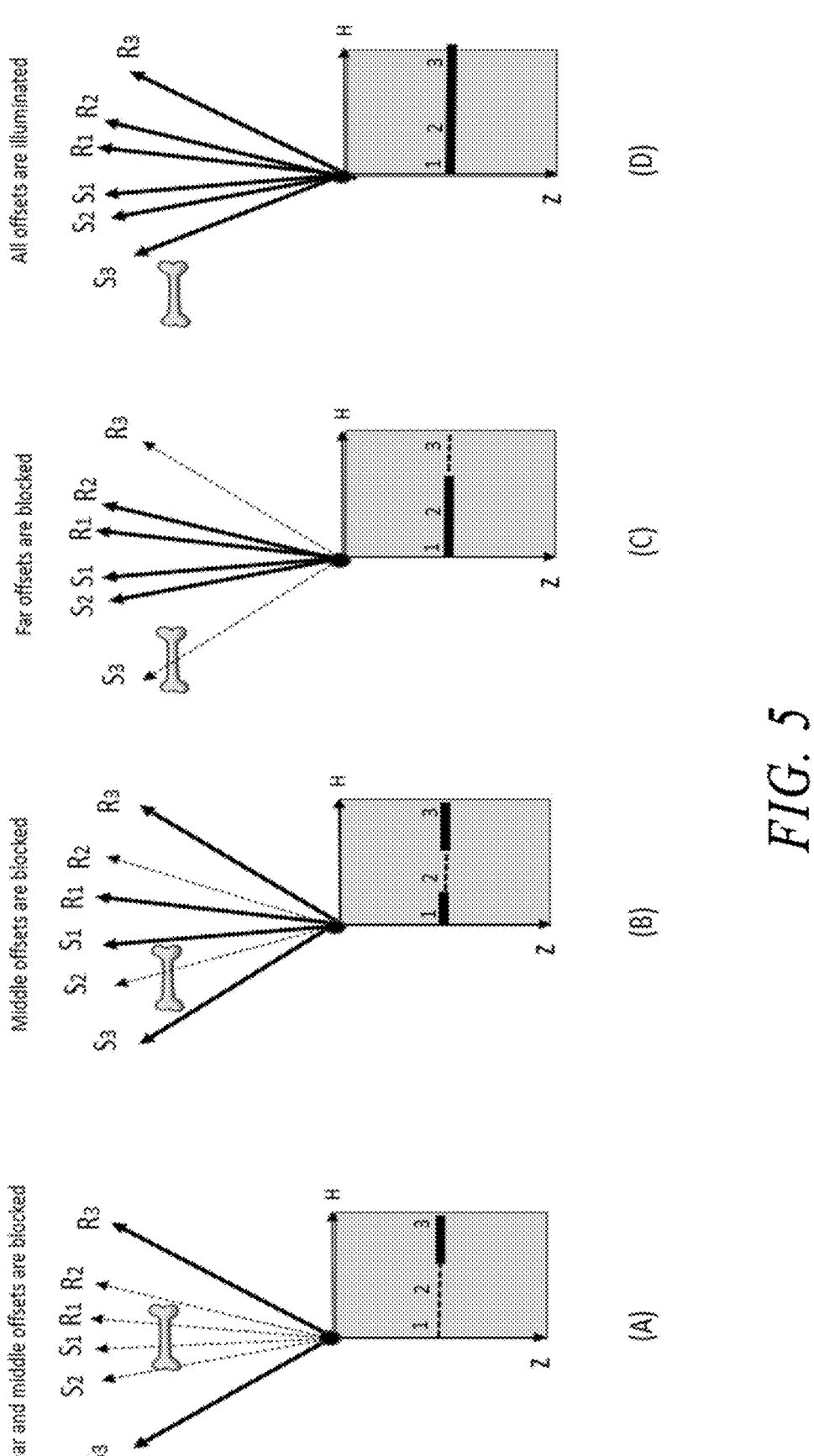
FIG. 5 depicts dim zones on common image point gathers and physical explanations of in-sonification differences at various transmitter-receiver offsets. (A) is the case where an output location is directly beneath a bone, (B) is the case where the output location is to the side of the bone, (C) is the case where the output location is away from the bone, and (D) is the case where the output location is far away from the bone. The solid dots denote the output point locations. On the common image point gathers the dash lines denote dim signals and the thick solid lines denote strong signals. $S_1$ and $R_1$ are a transmitter-receiver pair at near offset. $S_2$ and $R_2$ are a transmitter-receiver pair at middle offset. $S_3$ and $R_3$ are a transmitter-receiver pair at far offset.

It is important to point out that dim zones on common image point gathers are not fixed at certain offset or reflection angle range. They vary from location to location. For example, in FIG. 5 (A), directly beneath the center of a hard object the dim zone is seen on near offset traces while far offset traces receive full in-sonification via undershooting. A short distance outside the edge of the hard object (FIG. 5, B), the dim zone appears at the middle offset range because near offsets are not impacted by the hard object and far offsets are able to undershoot it. Farther away from the hard object (FIG. 5, C), the dim zone is at far offset range because one leg of a far offset ray path pair may be blocked by the hard object. If one moves even farther away from the hard object (FIG. 5, D), there will be no dim zone on a common image point gather because all offsets receive full in-sonification without any blockage by the hard object. All known coherent compounding methods are not able to make this important distinction [16-18].

Figure 6:
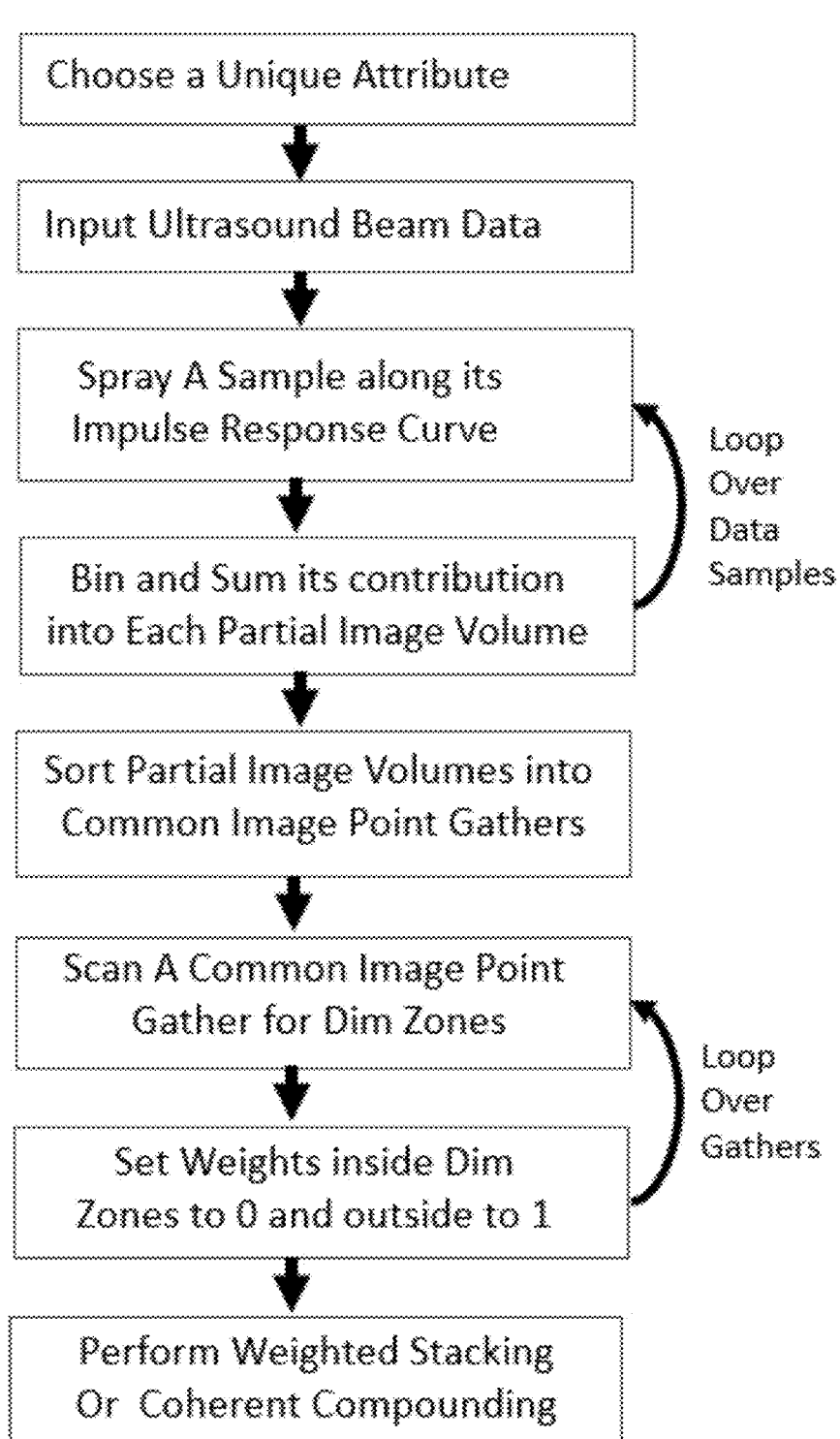
FIG. 6 is a workflow diagram of ultrasound imaging behind bones and/or hard objects.

The recommended implementation workflow in this disclosure includes the following steps (FIG. 6):

1. Decide a strategy for generating partial images and common image point gathers (i.e., binning and sorting in offset, reflection angle, or some other attribute).
2. Spray a data sample of an input ultrasound beam onto its impulse response curve in the image domain. A plurality of input ultrasound beams are sprayed, and each input ultrasound beam includes a plurality of data samples. For each point on the impulse response curve, determine a value of the unique attribute. Sum contribution of this data sample into all possible partial image volumes binned and sorted by the unique attribute.
3. Repeat step 2 for all data samples and all ultrasound beams.
4. Sort the partial image volumes into common image point gathers.
5. Scan all common image point gathers for dim zones. Set weights in dim zones to 0 and outside dim zones to 1 (or some other values in accordance with a weighting strategy)
6. Perform a weighted stacking of common image point gathers to produce the final image.

This workflow applies to all ultrasound data acquisition configurations: focused beam, divergent beam, planewave, synthetic aperture radar, and other beam types [15]. It also applies to all beamforming methods, possibly with significant modifications, so long as they are amenable to generation of desired common image point gathers. For example, we have disclosed in this publication a modification to the Kirchhoff integral method for generating common image point gathers for ultrasound beam data.

We typically use the distance between a transmitter and a receiver (i.e., offset) as a sorting attribute. We sometimes also use the reflection angle at an image point as another sorting attribute. If offset is used as the sorting attribute, the common image point gathers are called "offset gathers". If reflection angle is used as the sorting attribute, the common image point gathers are called "angle gathers". We have also disclosed in this publication ways to generate other types of common image point gathers ("other gathers").

Part III: Image Examples

3.1 Echo Data Simulation

Figure 7:
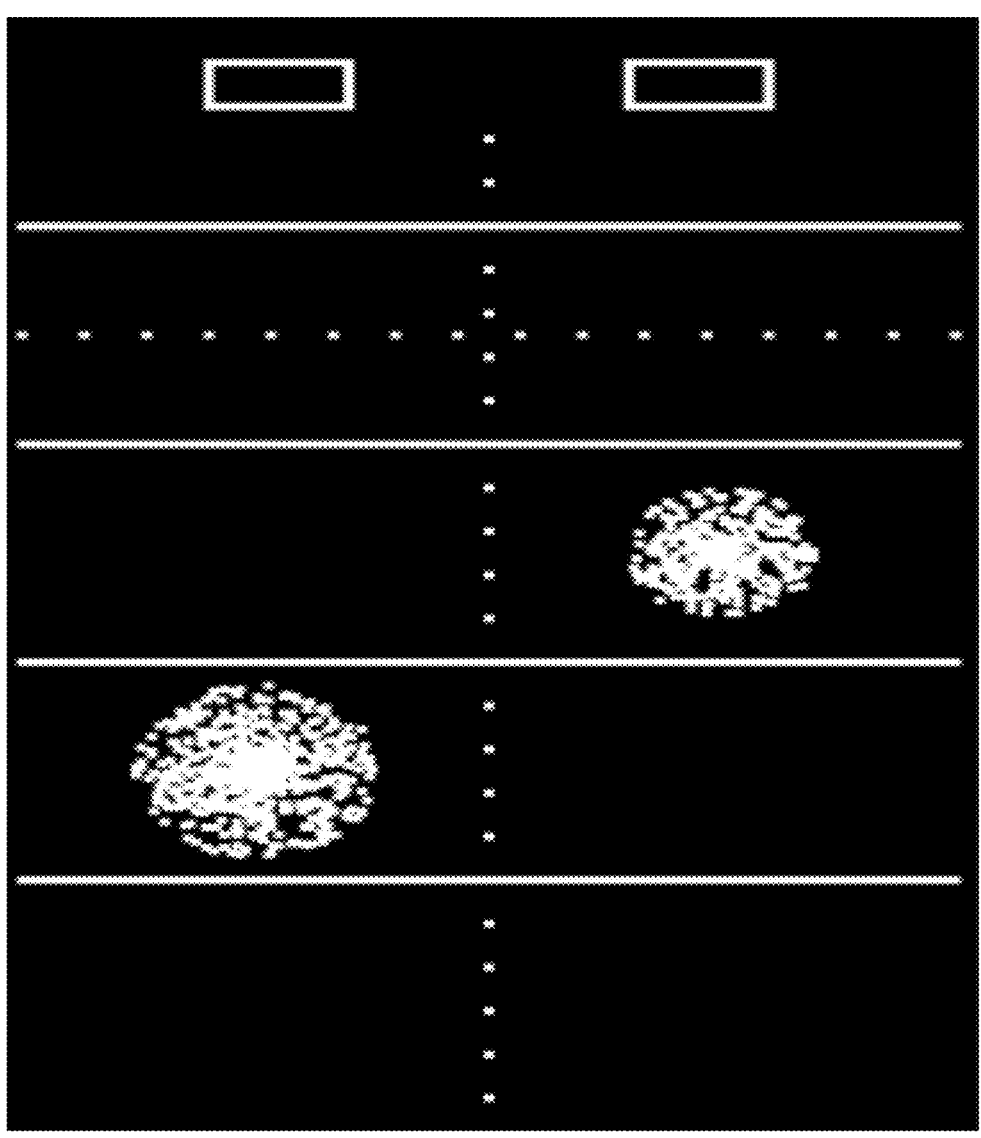
FIG. 7 shows a phantom model for the simulation: white dots are point scatters and white lines are continuous reflectors.

We use a modified version of Fresnel Simulator from Ultrasound Toolbox (USTB, https://www.ustb.co) for generation of numerical ultrasound beam data. The use of this simulator is subject to the citation rule. We sincerely thank the authors for making it available in the public domain [20]. The simulator is based on Fresnel approximation of diffraction of acoustic waves for rectangular transducers in a linear time invariant (LTI) system. Inputs to the simulator include a phantom model specification, a transducer specification, and a waveform specification. The phantom model used in this simulation contains (FIG. 7):

Two rectangular boxes with a depth range between 7-9 mm,

4 Flat continuous reflectors at 20 mm, 40 mm, 60 mm and 80 mm depth,

A hyperechoic target with 8 mm radius at 70 mm depth and a second hyperechoic target with 6 mm radius at 50 mm depth, A row of scatter points at 30 mm depth and a column of scatter points at the center of the model.

The transducer used in this simulation is a linear array with 192 elements (0.3 mm pitch) and each element has a width of 0.27 mm and a height of 5 mm. The central frequency of the simulated echo data is 3 MHz with 80% useful bandwidth and sampling frequency was 24 MHz. The two rectangular boxes at shallow depth in the phantom model are used to simulate the presence of bones by completely attenuating any and all reflections from deep tissues that travel through them (a kill operation in the simulation code).

Other transducers, for examples, transducers with 4 elements, 8 elements, 16 elements, 32 elements, 64 elements, 128 elements and 256 elements, can be used in accordance with the present application. Existing commercial linear phased array transducer used to image tissues and organs behind ribs is short in length so that it can only be placed in between rib bones along certain directions. In contrast, in the present application, transducers of different lengths can be used and be placed in any position and direction without fear of creating shadow zones in output images. Preferably, longer transducers (e.g., with 128, 256 or more elements) are used to achieve better resolution and signal to noise ratio.

Figure 8:
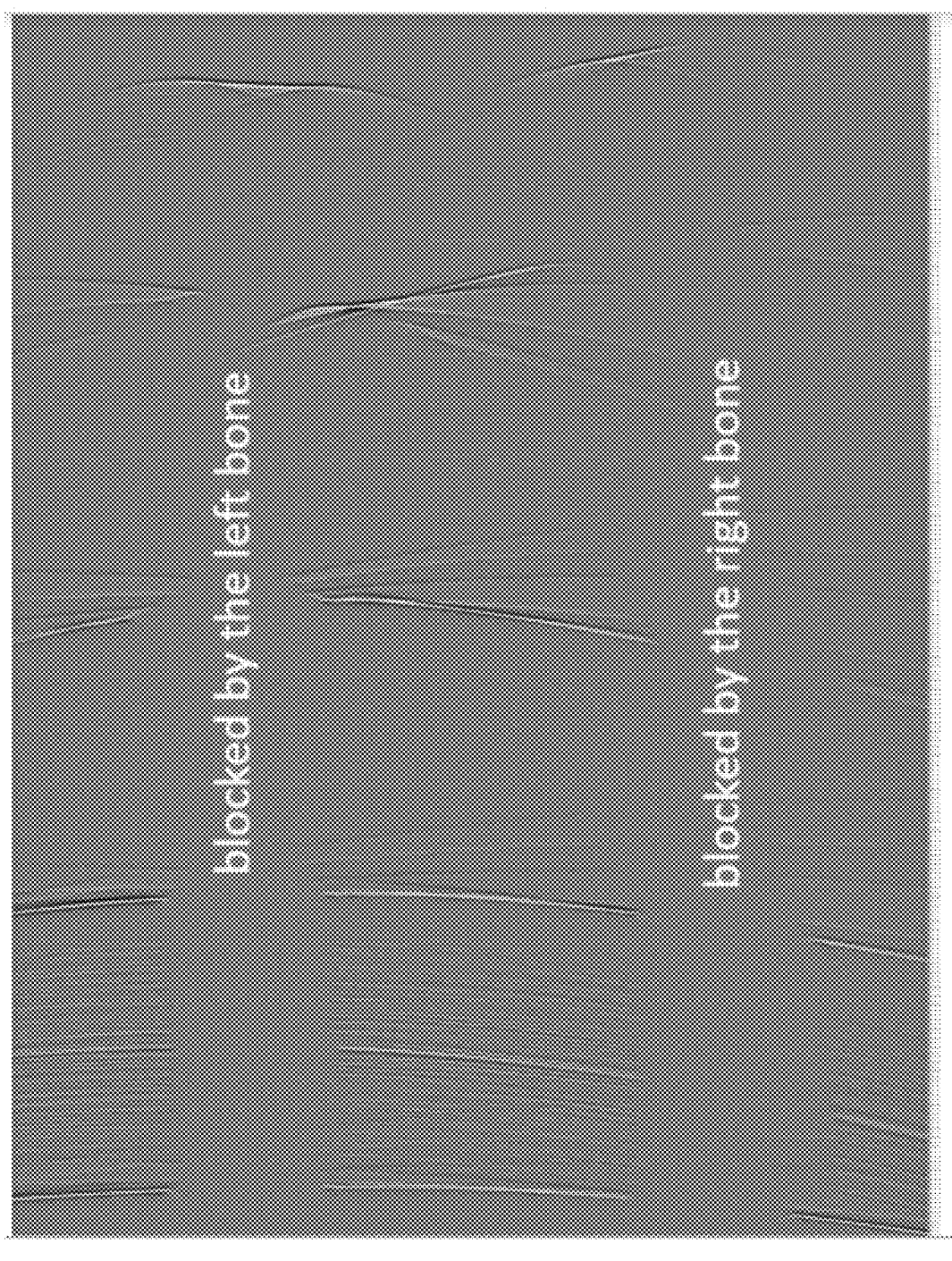
FIG. 8 shows a display of raw synthetic data for one beam at Xc=−9 mm.

We have simulated 384 focused beams using this phantom model. FIG. 8 shows a raw beam data at Xc=−9 mm. Since a long linear array is used in this simulation the receiver aperture is more than enough to cover the two bones (the rectangular boxes in FIG. 7). For early arrivals that travel above the two bones the beam data is continuous and well behaved. For arrivals that travel below the two bones the presence of bones on the raw beam data is clearly visible (two dim zones on input raw data): the left dim zone is caused by the shallow bone on the left; and the right dim zone is caused by the shallow bone on the right. In real data, inside the dim zones, there are some diffractions from the edges of the bones which are ignored in this simulation.

3.2 Image Comparison

Figure 9:
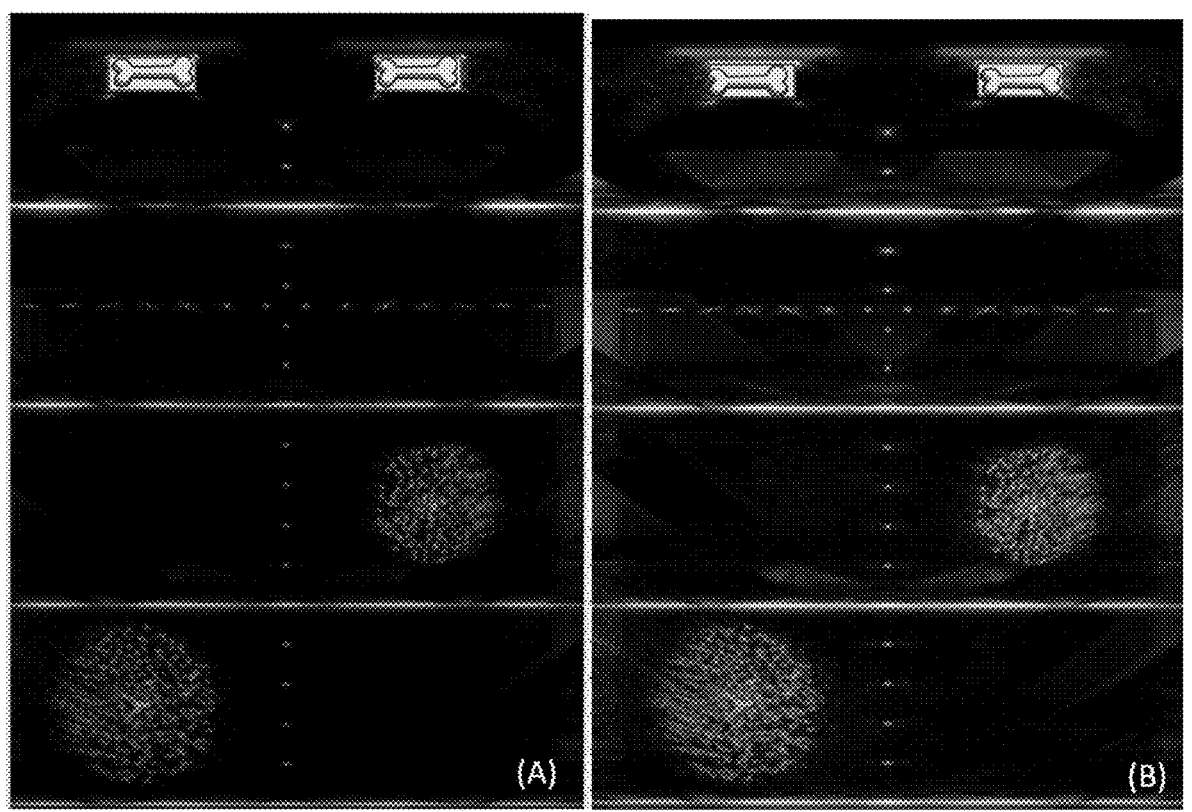
FIG. 9 shows the comparisons of two focused beam images using a linear array with 192 elements: Left (A) is from a pixel-based beamformer without any special processing. Right (B) is the same image with the optimal stacking method disclosed in this publication. All displays are in 60 dB with individual normalization.

FIG. 9 shows a comparison of two images of the same focused beam data. The imaging method and parameter settings are the same. The only difference is in the final stacking of common image point gathers. The left (A) is without special handling of the dim zones on the common image point gathers. The right (B) is with the proposed optimal stacking method that excludes or weighted down the dim zones. The image (B) is better than the image (A) below the shallow ribs: (1) the target reflectors are more continuous, and the target scatters are much stronger, and (2) the holes on the horizontal reflectors are largely filled.

REFERENCES

[1] Richard S. C. Cobbold (2007), Foundations of Biomedical Ultrasound, Oxford University Press, pages 431-437.

[2] O. H. Schuck (1957), Variable Focus Transducer, U.S. Pat. No. 3,090,030, May 14, 1963.

[3] B. S. Hertzberg and W. D. Middleton (2016), Ultrasound: The Requisites, The Third Edition, Elsevier. Chapter 1, pages 3-31. Also at expertconsult.com.

[4] A. Manbachi and R. S. C. Cobbold (2016), Ultrasound Array for Bone Sonography, U.S. patent application Ser. No. 14/893,642, Filed May 23, 2014.

[5] B. C. Byram, R. S. Hsi, and J. E. Tierney (2019), Advanced Ultrasound Imaging Techniques for Kidney Stone Detection and Characterization, U.S. patent application Ser. No. 16/432,731, Filed Jun. 5, 2019.

[6] S-W Huang, E. G. Radulescu, R. Q. Erkamp, S. Wang, K. E. Thiele, and D. Prater (2020), Rib Blockage Delineation in Anatomically Intelligent Echocardiography, U.S. patent application Ser. No. 16/836,985, filed Apr. 1, 2020.

[7] D. P. Duncan and M. G. Menon (2016), Shadow Suppression in Ultrasound Imaging, U.S. patent application Ser. No. 14/501,482, Filed Sep. 30, 2014.

[8] J. Hansegard and E. N. Steen (2014), Ultrasound Imaging System and Method for Identifying Data from a Shadow Region, U.S. patent application Ser. No. 13/731,531, Filed Dec. 31, 2012.

[9] R. E. Daigle (2009), Ultrasound Imaging System with Pixel Oriented Processing, U.S. Patent Application No. 2009/0112095 A1, Apr. 30, 2009.

[10] R. Zemp and M. F. Insana (2007), Imaging with Unfocused Regions of Focused Ultrasound Beams, J. Acoust. So. Amer. Vol. 121, pages 1491-1498.

[11] N. Q. Nguyen and Richard Q. Prager (2016), High-resolution Ultrasound Imaging with Unified Pixel-Based Beamforming, IEEE Transactions on Medical Imaging, Vol. 35, pages 98-108.

[12] O. M. H. Rindal (2019), Software Beamforming in Medical Ultrasound Imaging—a Blessing and a Curse, Ph.D. Thesis, University of Oslo.

[13] O. M. H. Rindal, A. Rodriguez-Molares, and A. Austeng (2018), A Simple, Artifact-free, Virtual Source Model, IEEE International Ultrasonics Symposium, IUS 1-4. https://doi.org/10.1109/ultsym.2018.8579944.

[14] D. J. Napolitano, B. D. DeBusschere, G. W. Mclaughlin, L. Y. Mo, C. H. Chou, T. L. Ji, R. W. Steins (2011), Continuous Transmit Focusing Method and Apparatus for Ultrasound Imaging Systems, U.S. Pat. No. 8,002,705, Issued August 2011.

[15] C. Peng, and J. Tang (2021), Acquisition and Processing of V-Wave Ultrasound Data Using a Linear or Curved Array Transducer, U.S. Patent Appl No. 63/184,174, Filed May 4, 2021.

[16] C. Y. Ahn (2011), Ultrasound System and Method for Providing an Ultrasound Spatial Compound Image Considering Steering Angle, U.S. patent application Ser. No. 12/874,125, Filed Sep. 1, 2010.

[17] R. C. Loftman, K. F. Ustuner and C. E. Bradley (2009), Coherent Image Formation for Dynamic Transmit Bemformation, U.S. patent application Ser. No. 12/477,783, Filed Jun. 3, 2009.

[18] V. Grau and J. A. Noble (2009), Method and Computer Program for Spatial Compounding of Images, U.S. patent application Ser. No. 11/988,657, Filed Jul. 14, 2006.

[19] O. Yilmaz (2011), Seismic Data Analysis: Processing, Inversion and Interpretation of Seismic Data, Society of Exploration Geophysicists.

[20] A. Rodriguez-Molares, Fresnel simulator, http://www.ustb.no/examples/fresnel/.

What is claimed is:

1. A method for imaging tissues behind obstacles comprising following steps:

(1) utilizing an ultrasound array transducer that includes at least four active elements and collecting a data sample of an ultrasound beam using the transducer;

(2) transmitting the data sample of the ultrasound beam of step (1) into image contributions along an impulse response curve in an output spatial image domain, each point on the impulse response curve has distinct values of attributes;

(3) determining a value of a unique attribute for the each point on the impulse response curve, and binning the each point on the impulse response curve by the value of the unique attribute;

(4) summing the value of the unique attribute in each bin for the each point on the impulse response curve into a corresponding partial image volume;

(5) repeating steps (2)-(4) for all data samples of all ultrasound beams to obtain a plurality of partial image volumes;

(6) generating common image point gathers by sorting the partial image volumes in increasing or decreasing value of the unique attribute; after generating the common image point gathers, scanning amplitude variations on each common image point gather and determining dim zones on the each common image point gather; and excluding or weighting down the dim zones in the common image point gathers or excluding or weighting down the dim zones in subsequent coherent compounding of the partial image volumes; and (7) obtaining an image of the tissues by stacking the common image point gathers, wherein the dim zones are caused by the obstacles.

2. The method of claim 1, wherein the ultrasound array transducer is a linear array transducer, a curved array transducer, or a phased array transducer.

3. The method of claim 1, wherein the ultrasound array transducer includes more than one row of active elements.

4. The method of claim 1, wherein the unique attribute is a transmitter-receiver distance on the ultrasound array transducer or a reflection angle at an image point.

5. The method of claim 1, wherein the unique attribute is a function of element positions on the ultrasound array transducer or scattering directions at an image point.

6. The method of claim 1, wherein the dim zones on the each common image point gather are caused by loss of transmitted energies when the ultrasound beam is blocked by the obstacles.

7. The method of claim 1, wherein the dim zones on the each common image point gather are determined by measuring an envelope amplitude, an acoustic energy level, or a signal coherency.

8. The method of claim 1, wherein the dim zones on the each partial image volume are caused by loss of transmitted energies when the ultrasound beam is blocked by the obstacles.

9. The method of claim 1, wherein the dim zones on a partial image volume are determined by measuring in envelope amplitude.

10. The method of claim 1, wherein the dim zones on the each partial image volume are determined by measuring an acoustic energy level or a signal coherency.

*  *  *  *  *